United States Patent [19]

Morozowich

[11] 4,080,506
[45] Mar. 21, 1978

[54] PHENACYL-TYPE ESTERS OF PGA₁ AND PGA₂

[75] Inventor: Walter Morozowich, Kalamazoo, Mich.

[73] Assignee: The Upjohn Company, Kalamazoo, Mich.

[21] Appl. No.: 497,242

[22] Filed: Aug. 14, 1974

[51] Int. Cl.² .............................................. C07C 177/00
[52] U.S. Cl. ..................................... 560/121; 424/317
[58] Field of Search ................................... 260/468 D

[56] References Cited

U.S. PATENT DOCUMENTS

| 3,729,502 | 4/1973 | Beal et al. | 260/468 |
| 3,984,454 | 10/1976 | Skubbula | 260/468 |

FOREIGN PATENT DOCUMENTS

| 2,322,655 | 11/1974 | Germany | 260/468 |

OTHER PUBLICATIONS

Fiesen et al., Reagents for Organic Synthesis, p. 1201 (1967).
McComie, Protective Groups in Organic Chemistry, p. 199 (1972).

Primary Examiner—Robert Gerstl
Attorney, Agent, or Firm—Morris L. Nielsen

[57] ABSTRACT

Phenacyl-type esters of PGA₁ and PGA₂ are disclosed, represented by the formula

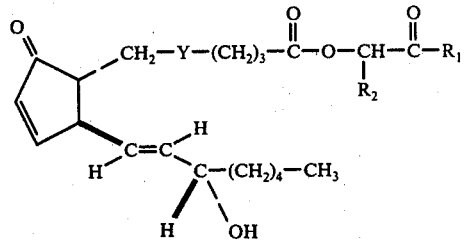

wherein $R_1$ is phenyl, p-bromophenyl, p-biphenylyl, p-nitrophenyl, p-benzamidophenyl, or 2-naphthyl; wherein $R_2$ is hydrogen or benzoyl; and wherein Y is $-CH_2CH_2-$ or cis$-CH=CH-$. The products are useful for the same pharmacological and medical purposes as the corresponding prostaglandins and analogs, and are also useful as a means of obtaining highly purified products.

18 Claims, No Drawings

PHENACYL-TYPE ESTERS OF PGA₁ AND PGA₂

BACKGROUND OF THE INVENTION

This invention relates to novel ester derivatives of prostaglandin A₁ (hereinafter identified as "PGA₁") and PGA₂, and to processes for producing them.

PGA₁ is represented by the formula

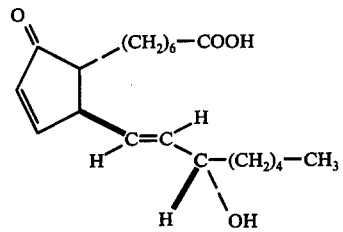   I

A systematic name for PGA₁ is 7-{2β-[(3S)-3-hydroxy-trans-1-octenyl]-5-oxo-3-cyclopentene-1α-yl}-heptanoic acid. PGA₁ is known to be useful for a variety of pharmacological and medical purposes, for example reduction and control of gastric secretion, and as a hypotensive agent to reduce blood pressure in mammals, including humans. See Bergstrom et al., Pharmacol. Rev. 20, 1 (1968) and references cited therein. As to racemic PGA₁, see for example P. W. Ramwell, Nature 221, 1251 (1969).

PGA₂ is represented by the formula:

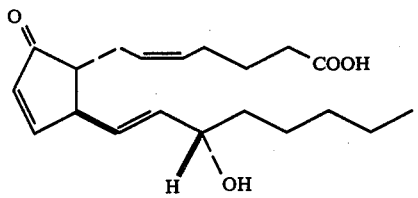   II

PGA₂ is available, as is also racemic PGA₂. See for example Bergstrom cited above, J. Martel et al., Tetr. Lett. 1491 (1972), and U.S. Pat. No. 3,759,965.

The above prostaglandin compounds are known to be useful for a variety of pharmacological and medical purposes, and the esters of this invention are useful for the same purposes.

Esters of the above compounds are known, wherein the hydrogen atom of the carboxyl group is replaced by a hydrocarbyl or substituted hydrocarbyl group. Among these are the methyl esters of PGA₁ and PGA₂ (J. P. Lee et al., Biochem. J. 105, 1251 (1967), the alkyl esters of one to 8 carbon atoms of PGA₂ (U.S. Pat. No. 3,759,965), and the decyl ester of PGA₂ (Belgian patent No. 765641, Derwent Farmdoc No. 67533S).

SUMMARY OF THE INVENTION

It is a purpose of this invention to provide novel ester derivatives of PGA₁ and PGA₂. It is a further purpose to provide such esters in a free-flowing crystalline form. It is still a further purpose to provide novel processes for preparing these esters.

The presently described phenacyl-type esters include compounds represented by the generic formula:

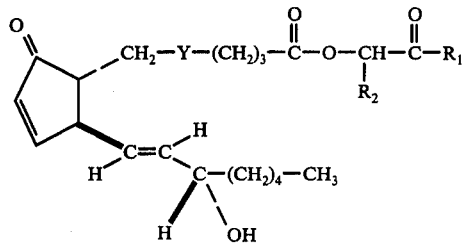   III wherein R₁ is phenyl, p-bromophenyl, p-biphenylyl, p-nitrophenyl, p-benzamidophenyl, or 2-naphthyl; wherein R₂ is hydrogen or benzoyl; and wherein Y is —CH₂CH₂— or cis—CH=CH—.

Accordingly, in the presently described esters, the group

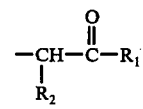

is exemplified by:

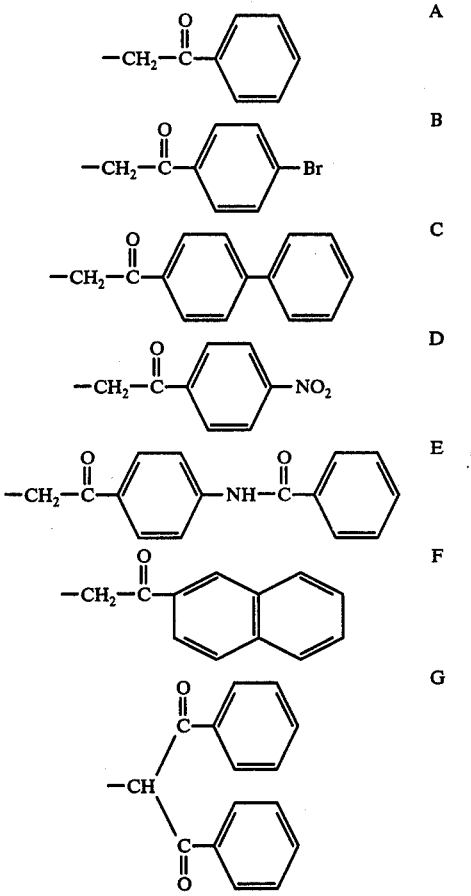

For example, PGA₁, phenacyl ester, is represented by formula III when Y is —CH₂CH₂, and

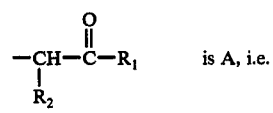   is A, i.e.

-continued

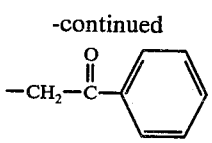

and is conveniently identified herein as the PGA$_1$ ester of formula III-A. Racemic compounds are designated by the prefix "racemic" or "dl"; when that prefix is absent, the intent is to designate an optically active compound. For example, racemic PGA$_2$, p-benzamidophenacyl ester, corresponds to formula III wherein Y is cis—CH=CH—, and

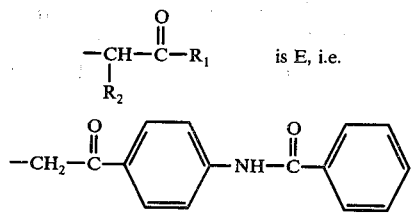

is E, i.e.

including of course not only the optically active isomer represented by formula III but also its enantiomer.

The novel formula-III compounds and corresponding racemic compounds of this invention are each useful for the same purposes as described above for PGA$_1$ and PGA$_2$ and are used for those purposes in the same manner known in the art, including oral, sublingual, buccal, rectal, intravaginal, intrauterine, or topical administration.

For many applications these novel prostaglandin esters which I have obtained from certain specified phenacyl-type halides have advantages over the corresponding known prostaglandin compounds. Thus, these phenacyl-type esters are surprisingly stable compounds having outstanding shelf-like and thermal stability. In contrast to the acid form of these prostaglandins, these esters are less subject to acid-catalyzed decomposition either by elimination of water or by epimerization. Thus these compounds have improved stability either in solid, liquid, or solution form. In oral administration these esters have shown surprisingly greater efficacy than the corresponding free acids or lower alkyl esters, whether because of longer duration of biological activity or because of improved lipophilicity and absorption is not certain. These esters offer a further advantage in that they have low solubility in water and the body fluids and are therefore retained longer at the site of administration.

A particularly outstanding advantage of many of these phenacyl-type esters is that they are obtained in free-flowing crystalline form, generally of moderately high melting point, in the range 50°–80° C. This form is especially desirable for ease of handling, administering, and purifying. These crystals are highly stable, for example showing practically no decomposition at accelerated storage tests, in comparison with liquid alkyl esters or the free acids. This quality is advantageous because the compound does not lose its potency and does not become contaminated with decomposition products.

These crystalline esters also provide a means of purifying PGA$_1$ and PGA$_2$, which are first converted to one of these esters, crystallized and recrystallized until pure, and then recovered as the free acid. One method of recovering the free acid is by enzymatic hydrolysis of the ester, for example with a lipase. See German Pat. No. 2,242,792, Derwent Farmdoc No. 23047U.

A p-iodophenacyl ester of 15(S)-15-methyl-PGF$_{2\alpha}$ was useful for X-ray crystallographic structure determination, E. W. Yankee et al., J. Am. Chem. Soc. 94, 3651 (1972). Various phenacyl esters have been useful for characterizing aliphatic acids because of their sharp melting points, Shriner and Fuson, "Systematic Identification of Organic Compounds," third Ed., pp. 154–157 (1948).

Especially preferred of the novel compounds of this invention are those compounds which are in free-flowing crystalline form, for example:
p-phenylphenacyl ester of PGA$_1$ and
p-benzamidophenacyl ester of PGA$_2$.

The phenacyl-type esters of PGA$_1$ and PGA$_2$ encompassed by formula III wherein

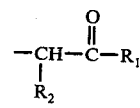

is defined by ester groups A through G are produced by the reactions and procedures described and exemplified hereinafter. For convenience, the prostaglandin or prostaglandin analog is referred to as "the PG compound." The term "phenacyl" is used in a generic sense, including also substituted phenyl and naphthyl derivatives.

Various methods are available for preparing these esters. Thus, by one method, the PG compound is converted to a sodium salt by methods known in the art and reacted with an appropriate phenacyl halide in a solvent.

Preferred, however, is the method of simply mixing the PG compound with a phenacyl halide, preferably the bromide, and a tertiary amine in a solvent and letting the reaction proceed at room temperature (about 20° to 30° C.). The course of the reaction is readily followed by sampling the mixture and subjecting the samples to thin layer chromatography, usually being complete within 0.25–4.0 hr. Thereafter the reaction mixture is worked up to yield the ester following methods described herein or known in the art, for example the product being purified by silica gel chromatography.

Examples of the phenacyl-type halides useful for this purpose are: phenacyl bromide, p-bromophenacyl bromide, p-phenylphenacyl bromide, p-nitrophenacyl bromide, p-benzamidophenacyl bromide, 2-bromo-2'-acetonaphthone, and 2-bromo-1,3-diphenyl-1,3-propanedione. In using these reagents the usual precautions are taken to avoid their lachrymatory effects.

Examples of suitable tertiary amines are triethylamine, diethylmethylamine, diisopropylethylamine, dimethylisobutylamine, and dimethylaniline.

Examples of suitable solvents are acetonitrile, dioxane, and tetrahydrofuran, N,N-dimethylformamide, and dimethylsulfoxide.

The phenacyl halide is preferably used in equivalent amounts or in excess to insure that all of the PG compound is converted to ester. Excess phenacyl halide is separated from the product by methods described herein or known in the art, for example by chromatography.

Solid esters are converted to a free-flowing crystalline form on crystallization from a variety of solvents, including ethyl acetate, tetrahydrofuran, methanol, ethanol, and acetone, by cooling or evaporating a saturated solution of the ester in the solvent or by adding a miscible non-solvent such as diethyl ether, hexane, or water. The crystals are then collected by conventional techniques, e.g. filtration or centrifugation, washed with a small amount of solvent, and dried under reduced pressure. They may be dried in a current of warm nitrogen or argon, or by warming above 45° C., taking care not to exceed the melting point. Although the crystals are normally pure enough for many applications, they may be recrystallized by the same general techniques to achieve improved purity after each recrystallization.

DESCRIPTION OF THE PREFERRED EMBODIMENTS

The invention can be more fully understood by the following examples.

All temperatures are in ° C.

Silica gel chromatography, as used herein, is understood to include chromatography on a column packed with silica gel, elution, collection of fractions, and combination of those fractions shown by thin layer chromatography (TLC) to contain the desired product free of starting material and impurities.

"TLC," herein, refers to thin layer chromatography.

EXAMPLE 1

PGA$_1$, p-Phenylphenacyl Ester (Formula III-C wherein Y is —CH$_2$CH$_2$—).

A mixture of PGA$_1$ (0.50 g.), p-phenylphenacyl bromide (0.575 g.), and 0.36 ml. of diisopropylethylamine in 10 ml. of acetonitrile is left standing at about 25° C. for about 16 hr. The mixture is concentrated under reduced pressure and the residue is subjected to silica gel chromatography, eluting with ethyl acetate-hexane (3:7) followed by ethyl acetate-hexane (1:1). The residue obtained by concentration of selected fractions is crystallized from ethyl acetate-hexane as the title compound, free-flowing crystals, 0.4 g. m.p. 51.3°–51.8° C., having R$_f$ 0.5 (TLC on silica gel in ethyl acetate-hexane (1:1)).

EXAMPLES 2–7

Following the procedures of Example 1 but replacing p-phenylphenacyl bromide of that example with the phenacyl halides listed below in Table I, the corresponding esters of PGA$_1$ are obtained.

Likewise following the procedures of Examples 1–7 but employing racemic PGA$_1$, there are obtained the corresponding esters of racemic PGA$_1$.

TABLE I

Esters of PGA$_1$
(Refer to formula III wherein Y is —CH$_2$CH$_2$—).

| Example | Phenacyl Halide | Product of PGA$_1$ esters of formula: |
| --- | --- | --- |
| 2 | phenacyl bromide | III-A |
| 3 | p-bromophenacyl bromide | III-B |
| 4 | p-nitrophenacyl bromide | III-D |
| 5 | p-benzamidophenacyl bromide | III-E |
| 6 | 2-bromo-2'-acetonaphthone | III-F |
| 7 | 2-bromo-1,3-diphenyl-1,3-propanedione | III-G |

EXAMPLE 8

PGA$_2$, p-Phenylphenacyl Ester (Formula III-C wherein Y is cis—CH=CH—).

A mixture of PGA$_2$ (0.67 g.), p-phenylphenacyl bromide (0.60 g.) and 0.26 ml. of diisopropylethylamine in 10 ml. of acetonitrile is left standing at about 25° C. for about 16 hr. The mixture is concentrated under reduced pressure and subjected to silica gel chromatography, eluting with 2% tetrahydrofuran in chloroform. The residue obtained by concentration of selected fractions is the title compound, 0.535 g., a colorless oil, having R$_f$ 0.5 (TLC on silica gel in ethylacetate-hexane (6:4)), and mass spectral peaks at 600, 529, and 510.

EXAMPLE 9

PGA$_2$, p-Benzamidophenacyl Ester (Formula III-E wherein Y is cis—CH=CH—).

Following the procedure of Example 8 but using 0.35 g. of PGA$_2$, 0.46 g. of p-benzomidophenacyl bromide, and 0.50 ml. of diisopropylethylamine in 10 ml. of acetonitrile, there is obtained a crude residue. This residue is subjected to silica gel chromatography, eluting with ethyl acetate-hexane (7:3) to yield an oil. This oil is crystallized from ethyl acetate-hexane as the title compound, 0.24 g., pale yellow free-flowing crystals, m.p. 74.7°–75.2° C., having R$_f$ 0.4 (TLC on silica gel in ethyl acetate-hexane (6:4)).

EXAMPLES 10–14

Following the procedures of Example 8 but replacing p-phenylphenacyl bromide of that example with the phenacyl halides listed below in Table II, the corresponding esters of PGA$_2$ are obtained.

Likewise following the procedures of Example 8–14 but employing racemic PGA$_2$, there are obtained the corresponding esters of racemic PGA$_2$.

TABLE II

Esters of PGA$_2$
(Refer to formula III wherein Y is cis-CH=CH—).

| Example | Phenacyl Halide | Product PGA$_2$ esters of formula: |
| --- | --- | --- |
| 10 | phenacyl bromide | III-A |
| 11 | p-bromophenacyl bromide | III-B |
| 12 | p-nitrophenacyl bromide | III-D |
| 13 | 2-bromo-2'-acetonaphthone | III-F |
| 14 | 2-bromo-1,3-diphenyl-1,3-propanedione | III-G |

I claim:

1. An optically active compound of the formula:

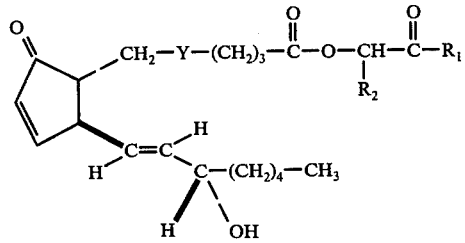

wherein R$_1$ is phenyl, p-bromophenyl, p-biphenylyl, p-nitrophenyl, p-benzamidophenyl, or 2-naphthyl; wherein R$_2$ is hydrogen or benzoyl; and wherein Y is —CH$_2$CH$_2$— or cis—CH=CH—.

2. A compound according to claim 1 wherein Y is —CH$_2$CH$_2$—.

3. The phenacyl ester of PGA$_1$, a compound according to claim 2.

4. The p-phenylphenacyl ester of PGA$_1$, a compound according to claim 2.

5. The p-nitrophenacyl ester of PGA$_1$, a compound according to claim 2.

6. The p-benzamidophenacyl ester of PGA$_1$, a compound according to claim 2.

7. The 2-naphthoylmethyl ester of PGA$_1$, a compound according to claim 2.

8. The α-benzoylphenacyl ester of PGA$_1$, a compound according to claim 2.

9. A compound according to claim 1 wherein Y is a cis—CH=CH—.

10. The phenacyl ester of PGA$_2$, a compound according to claim 9.

11. The p-phenylphenacyl ester of PGA$_2$, a compound according to claim 9.

12. The p-nitrophenacyl ester of PGA$_2$, a compound according to claim 9.

13. The p-benzamidophenacyl ester of PGA$_2$, a compound according to claim 9.

14. The 2-naphthoylmethyl ester of PGA$_2$, a compound according to claim 9.

15. The α-benzoylphenacyl ester of PGA$_2$, a compound according to claim 9.

16. Free-flowing crystals of a compound of the formula:

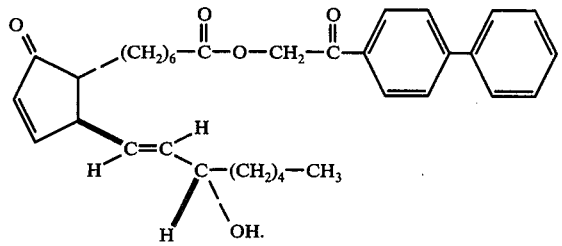

17. Free-flowing crystals of a compound of the formula:

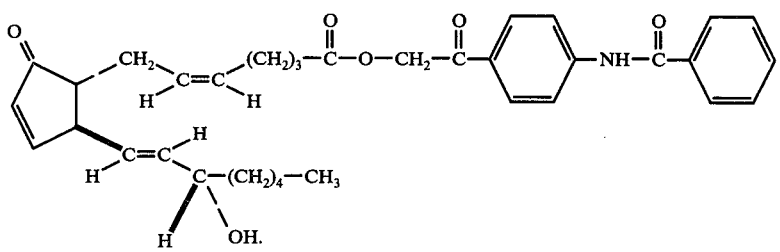

18. An optically active compound of the formula

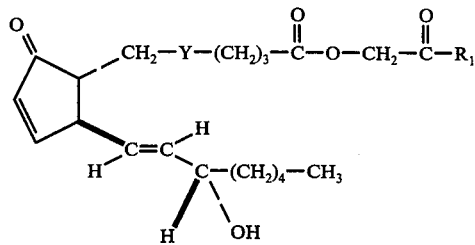

wherein R$_1$ is phenyl, p-bromophenyl, p-biphenylyl, p-nitrophenyl, p-benzamidophenyl, or 2-naphthyl; and wherein Y is —CH$_2$CH$_2$— or cis—CH=CH—.

* * * * *